United States Patent [19]

Miller et al.

[11] 4,160,084

[45] Jul. 3, 1979

[54] METHOD FOR THE SEPARATION OF ANTIBIOTIC MACROLIDES

[75] Inventors: Thomas W. Miller, Carteret; Kenneth E. Wilson, Woodbridge; Robert E. Ormond, Edison, all of N.J.

[73] Assignee: Merck & Co., Inc., Rahway, N.J.

[21] Appl. No.: 840,921

[22] Filed: Oct. 11, 1977

[51] Int. Cl.$^2$ ............................................. C07H 17/08
[52] U.S. Cl. .................................. 536/17 A; 435/119; 424/181; 435/886
[58] Field of Search ...................... 260/343.41; 536/17

[56] References Cited

U.S. PATENT DOCUMENTS 3,950,360  4/1976  Aoki et al. ...................... 260/343.41

OTHER PUBLICATIONS

Mishima et al., Tetrahedron Letters, No. 10, pp. 711–714, 1975.
Journal of Antibiotics 29(6), Jun. 1976, pp. 76—35 to 76—42 and pp. 76—14 to 76—16.

*Primary Examiner*—Natalie Trousof
*Assistant Examiner*—Jane T. Fan
*Attorney, Agent, or Firm*—David L. Rose; Richard A. Thompson; Harry E. Westlake

[57] ABSTRACT

This case relates to a novel process which aids in the isolation and purification of novel compounds which are produced by the microorganism, *Streptomyces avermitilis*. The process described utilizes a column containing a hydroxyalkylated dextran gel as a step in the separation of the desired compounds. The compounds which are isolated and purified are described generically as C-076 and have significant parasiticidal activity.

6 Claims, No Drawings

METHOD FOR THE SEPARATION OF ANTIBIOTIC MACROLIDES

SUMMARY OF THE INVENTION

This invention is directed to a process for isolating the novel chemical compounds C-076 which are produced by the fermentation of a nutrient medium with a strain of the microorganism, *Streptomyces avermitilis*.

The compounds, to which the novel techniques of isolation and purification of this invention are directed, are described in co-pending U.S. application Ser. No. 772,601 of G. Albers-Schonberg, R. Burg, T. Miller, R. Ormond and H. Wallich. Said application teaches the use and characterization of the C-076 compounds as well as the utilization and characterization of the microorganism, *Streptomyces avermitilis*. Said application is hereby incorporated by reference in this application.

More particularly, this invention is comprised of a novel technique wherein it is an object of this process to aid in the isolation of the parasiticidal active compound in a substantially purified form. Further objects of this invention will become apparent from the following description.

DESCRIPTION OF THE INVENTION

In accordance with this invention, novel techniques of extraction and fractionation are utilized to isolate and purify substances generically described herein as C-076. These substances are prepared by growing under controlled conditions strains of microorganisms of *Streptomyces avermitilis*. These substances are described as C-076 A1a, A1b, A2a, A2b, B1a, B1b, B2a, and B2b.

Based on taxonomic studies, the microorganisms capable of producing these C-076 compounds are of a new species of the genus Streptomyces, which has been named *Streptomyces avermitilis*. One such culture, isolated from soil is designated MA-4680 in the culture collection of MERCK & CO., Inc., Rahway, New Jersey. A C-076 producing sample of this culture has been deposited in the permanent culture collection of the Fermentation Section of the Northern Utilization Research Branch, U.S. Department of Agriculture at Peoria, Illinois, and has been assigned the accession number NRRL 8165. A sample of NRRL 8165 has also been deposited, without restriction as to availability, in the permanent culture collection of the American Type Culture Collection at 12301 Parklawn Drive, Rockville, Maryland 20852, and has been assigned the accession number ATCC 31,267.

However, the present invention also embraces mutants of the above described microorganism. For example, those C-076 producing mutants which are obtained by natural selection or those produced by mutating agents including X-ray irradiation, ultraviolet irradiation, nitrogen mustard or like treatments are also included within the ambit of this invention.

One example of such an organism is a strain of *Streptomyces avermitilis* MA 4848 which was isolated after irradiation with ultraviolet light of *Streptomyces avermitillis* MA 4680. A lyophilized tube and a frozen vial of this culture has been deposited in the permanent culture collection of the American Type Culture Collection, and they have been assigned the accession numbers 31272 and 31271 respectively. Slightly higher fermentation yields of C-076 have been obtained using this frozen stock as inoculum.

In particular, this invention is directed to a method for the separation of C-076 B1 B2 components wherein a solution containing C-076 B1 B2 components is chromatographed on a column containing hydroxyalkylated dextran gel and eluting said column. The solvent utilized in the elution step is a mixture of lower boiling hydrocarbons:monoaromatics:lower alcohols in the proportions of about 30–90%:10–60%:5–25% and recovering said components.

This invention also includes the process wherein C-076 A1, A2 components are separated by chromatographing on a column containing hydroxyalkylated dextran gel and eluting said column. The solvent utilized in the elution step is a mixture of low boiling hydrocarbons:monoaromatics:lower alcohols in the ratio of about 5–7:0.5–1.5:0.5–1.50 and recovering said components.

By the term, "lowering boiling hydrocarbons" is meant hydrocarbons having from 5 to about 8 carbon atoms wherein such carbon atoms may be a straight or branched chain. Illustrative of such low boiling hydrocarbons are pentane, hexane, heptane, octane, isopentane and the like.

By the term, "monoaromatic" is meant monocyclic aromatic compounds which may contain one or more lower alkyl substituent. Illustrative of such monoarmomatic compounds are toluene, benzene, xylene and the like.

By the term, "lower alcohol" is meant alcohols having from 1 to about 3 carbon atoms. Illustrative of such lower alcohols are methanol, ethanol, propanol, isopropanol and the like.

Although the elution solvent mixtures and proportions may be utilized over a fairly wide range in the separation of the B1 and B2 components, a more narrow range is usually utilized for optimum separation of the components. Thus, the case of the separation of B1 and B2 components, a more preferred solvent mixture and proportions are hexane:toluene:methanol in a ratio of about 3:1:1.

Also, in the separation of the A1 compound from the A2 component, a preferred solvent mixture and ratio will result in a more desirous separation. Thus, in the case of A1 A2, a more preferred solvent mixture and ratio is hexane:toluene:methanol in a ratio of 6:1:1.

The C-076 compounds are produced during the aerobic fermentation of suitable aqueous nutrient media under conditions described hereinafter, with a producing strain of *Streptomyces avermitilis*. Aqueous media such as those used for the production of many antibiotic substances are suitable for use in this process for the preparation of C-076.

Such nutrient media contain sources of carbon and nitrogen assimilable by the microorganism and generally low levels of inorganic salts. In addition, the fermentation media may contain traces of metals necessary for the growth of the microorganisms. These are usually present in sufficient concentration in the complex sources of carbon and nitrogen which may be used as nutrient sources, but can, of course, be added separately to the medium if desired.

In general, carbohydrates such as sugars, for example dextrose, sucrose, maltose, lactose, dextran, cerelose and the like, and starches are suitable sources of assimilable carbon in the nutrient media. The exact quantity of the carbon source which is utilized in the medium will depend, in part, upon the other ingredients in the medium but it is usually found that an amount of carbohydrate between about 0.5 and 5% by weight of the medium is satisfactory. These carbon sources can be used individually or several such carbon sources may be combined in the same medium.

Various nitrogen surces such as yeast hydrolysates, yeast autolysate, soybean meal, casein hydrolysates, yeast extracts, corn steep liquors, distillers solubles, cottonseed meal, meat extract and the like, are readily assimilable by Streptomyces avermitilis in the production of the C-076 compounds. The various sources of nitrogen can be used alone or in combination in amounts ranging from about 0.2 to 6% by weight of the medium.

Among the nutrient inorganic salts which can be incorporated in the culture media are the customary salts capable of yielding sodium, potassium, magnesium, ammonium calcium, phosphate, sulfate, chloride, carbonate and like ions. Also included are trace metals such as cobalt, manganese, iron and the like.

The fermentation employing the C-076-producing microorganisms can be conducted at temperatures ranging from about 20° C. to about 40° C. For optimum results, it is most convenient to conduct these fermentations at a temperature in the range of from about 24° C. to about 30° C. Temperatures of about 27° C.-28° C. are most preferred. The pH of the nutrient medium suitable for producing the C-076 compounds can vary from about 5.0 to 9.0 with a preferred range of from about 6.0 to 7.5.

Small scale fermentations are conveniently carried out by placing suitable quantities of nutrient medium in a flask employing known sterile techniques, inoculating the flask with either spores or vegetative cellular growth of a C-076-producing strain of Streptomyces avermitilis, loosely stoppering the necks of the flask with cotton, and permitting the fermentation to proceed in a constant room temperature of about 28° C. on a rotary shaker for about 3 to 10 days. For larger scale work, it is preferable to conduct the fermentation in suitable tanks provided with an agitator and a means of aerating the fermentation medium. The nutrient medium is made up in the tank and after sterilization is inoculated with a suitable source of vegetative cellular growth of a C-076 producing strain of Streptomyces avermitilis. The fermentation is allowed to continue for from 1 to 8 days while agitating and/or aerating the nutrient medium at a temperature in the range of from about 24° C. to 37° C. The degree of aeration is dependent upon several factors such as the size of the fermentor, agitation speed and the like. Generally, the larger scale fermentations are agitated at about 95 to 150 rpm and about 2 to 20 cubic feet per minute of air.

The substances of this invention, which are generially referred to herein as C-076, are found primarily in the mycelium on termination of the Streptomyces avermilitilis fermentation, and may be recovered and separated from one another as described below. Four major and four minor components of the C-076 as elaborated by Streptomyces avermitilis have been isolated. The eight different compounds are identified herein as C-076 A1a, A1b, A2a, A2b, B1a, B1b, B2a and B2b.

Based on experimental data, the C-076 compounds are believed to have the following planar structural formula:

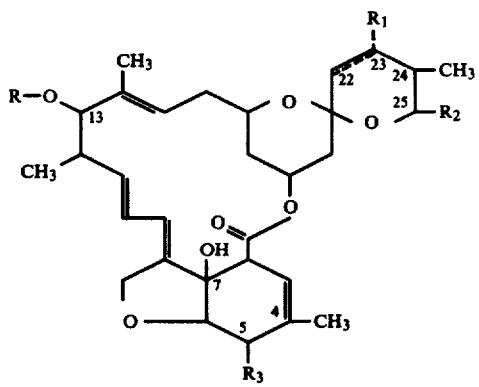

wherein R is the α-L-oleandrosyl-α-L-oleandroside of the structure:

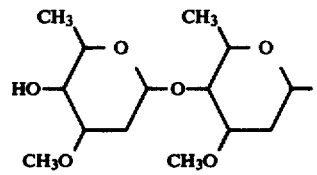

and wherein the broken line indicates a single or a double bond; $R_1$ is hydroxy and is present only when said broken line indicates a single bond.
$R_2$ is propyl or butyl; and
$R_3$ is methoxy or hydroxy.

In the foregoing structural formula, the individual compounds are as set forth in Table IV.

TABLE IV

|     | $R_1$       | $R_2$  | $R_3$  |
|-----|-------------|--------|--------|
| A1a | Double bond | butyl  | -OCH₃  |
| A1b | Double bond | propyl | -OCH₃  |
| A2a | -OH         | butyl  | -OCH₃  |
| A2b | -OH         | propyl | -OCH₃  |
| B1a | Double bond | butyl  | -OH    |
| B1b | Double bond | propyl | -OH    |
| B2a | -OH         | butyl  | -OH    |
| B2b | -OH         | propyl | -OH    |

The major C-076 compounds are not produced in equal amounts by the fermentations described herein. In general, it has been found that the A1 compounds comprise about 20 to 30% by weight of the total C-076 complex produced, the A2 compounds about 1 to 20 % and the B1 and B2 compounds each about 25 to 35%.

The separation of the C-076 series of compounds from the whole fermentation broth and the recovery of the individual components is carried out by solvent extraction and application of chromatographic fractionations with various chromatographic techniques and solvent systems.

The C-076 compounds have slight solubility in water, but are soluble in organic solvents. This property may be conveniently employed to recover them from the fermentation broth. Thus in one recovery method, the whole fermentation broth is filtered and the aqueous filtrate discarded. The wet mycelial cake is then extracted with an appropriate organic solvent. While any organic solvent may be employed, it is preferable to use a water miscible solvent such as acetone, methanol, ethanol and the like. Generally, several extractions are desirable to achieve maximum recovery. The solvent removes the C-076 active components as well as other substances lacking the antiparasitic activity of C-076. If the solvent is a water miscible one, the water is also removed from the wet mycelia. The extracted mycelia may be discarded. The solvent extracts are evaporated to remove the organic solvent and extracted several times with a second solvent. When the first extraction employs a water miscible solvent, the second extraction preferably employs a water immiscible solvent such as chloroform, methylene chloride, carbon tetrachloride, ethylacetate, methylethyl ketone, methylisobutyl ketone and the like. These latter extracts are dried and concentrated using known techniques to afford a residue comprising C-076 admixed with other materials. This fraction is then conveniently chromatographed in order to separate the active C-076 compounds from other material and also to separate and isolate the individual C-076 compounds. The chromatographic techniques which may be employed to purify the C-076 compounds are generally known to those skilled in this art. Examples of such techniques are column chromatography, using such media as silica gel, aluminum oxide, dextran gels and the like, and elution of such columns with various solvents, and/or a combination of two or more solvents, in varying ratios. Liquid chromatography is employed for the detection of the C-076 compounds, and high pressure liquid chromatography may be employed to isolate purified fractions containing one or more of such compounds. Likewise, thin layer chromatography may be employed to detect the presence of, and to isolate the individual C-076 compounds,. The use of the foregoing techniques as well as others known to those skilled in this art, will afford purified compositions comprising the C-076 compounds as well as the individual C-076 compounds themselves.

The following examples are capable of wide variation and modification and any minor departure or extension is considered as being within the skill of the artisan and as falling within the scope of this invention.

EXAMPLE 1

A 250-ml. baffled Erlenmeyer flask containing 50 ml. of the following medium:
Lactose: 2.0%
Distiller's Solubles: 1.5%
Autolyzed yeast, Ardamine pH: 0.5%
pH—before sterilization: 7.0 is inoculated with the contents of one frozen vial of *Streptomyces avermitilis* MA-4848 and incubated on a rotary shaker at 28° C. for 24 hours at 150 rmp.

Ten ml. of the above fermentation medium is employed to inoculate 500 ml. of the same medium as above in a 2-liter baffled Erlenmeyer flask. The fermentation medium is incubated at 150 rpm on a rotary shaker at 28° C. for 24 hours.

All of the foregoing medium is employed to inoculate 467 liters of the following medium in a 756-liter stainless steel fermentor:
Lactose: 2.0%
Distiller's Solubles: 1.5%
Autolyzed yeast, Ardamine pH: 0.5%
Polyglycol 2000: 0.32 ml./liter
pH—before sterilization: 7.0

The fermentation medium is incubated at 28° C. for 40 hours with an air flow of 10 cubic feet per minute and an agitation rate of 130 rpm.

230 Liters of the above medium is employed to inoculate 4,310 liters of the following medium in a 5,670-liter stainless steel fermentor:
Dextrose: 4.5%
Peptonized Milk: 2.4%
Autolyzed yeast, Ardamine pH: 0.25%
Polyglycol 2000: 2.5 ml./liter
pH—before sterilizaton: 7.0

The fermentation continues for 144 hours at 26° C. with an air flow rate of 54.3 cubic feet per minute and agitation rate of 120 rpm.

The fermentation medium is filtered and the mycelial filter cake washed with about 550 liters of water, the filtrate and washings are discarded. The filter cake is agitated with about 1500 liters of acetone for about one hour and filtered. The filter cake is washed with a mixture of about 150 liters of acetone and 40 liters of deionized water affording about 2000 liters of extract.

The foregoing fermentation and extraction is repeated on the same scale affording a further 2000 liters of acetone extract which is combined with the first extract and evaporated to a volume of about 800 liters. The pH of the concentrate is adjusted to about 4.7 with concentrated hydrochloric acid and combined with about 800 liters of methylene chloride. The combined solvents are agitated for about 4 hours and separated. The aqueous layer is combined with an additional 800 liters of methylene chloride and agitated for about 4 hours. The layers are separated and each methylene chloride extract separately treated with about 10 kilograms of Super-Cel and filtered. Both extracts are evaporated to a combined volume of about 60 liters.

EXAMPLE 2

The 60-liter solution of C-076 in methylene chloride of the previous example is concentrated to dryness in vacuo and the residue in combined three times with 60 liter portions of methanol and evaporated to dryness to remove any residual methylene chloride. The final methanol concentrate volume is approximately 36 liters. The methanol solution is stored overnight and filtered. The filter cake is washed with 40 liters of fresh methanol and the methanol filtrates and washings are combined. The methanol solution is combined with 95 liters of ethylene glycol and 130 liters of heptane. The 2-layer solution is agitated for 5 minutes and the lower layer (ethylene glycol and methanol) is separated. The heptane solution is washed with a mixture of 20 liters of ethylene glycol and 6.3 liters of methanol. After 5 minutes of agitation, the lower layer is separated and combined with the first ethylene glycol/methanol extract. An equal volume of water (approximately 150 liters) containing 79 g. of salt per liter is added to the ethylene glycol/methanol extracts. This solution is extracted with 150 liters of ethyl ether with agitation for 5 minutes. The ether layer is washed with 75 liters of water (½ volume) and agitated for 5 minutes and the layers separated. This procedure is repeated an additional 2 times (the final water wash contains 20 g. of salt per liter) affording a final ether layer volume of 110 liters. The ether layer is concentrated in vacuo, to a minimum volume, keeping the temperature less than 25° C. Forty liters of methylene chloride is added to the residue and the solution is evaporated to dryness. This procedure is repeated and the final residue concentrated in vacuo at 50° C. to dryness.

EXAMPLE 3

A sample of 150 g. of crude C-076 is dissolved in 3 liters of a solvent mixture of hexane:toluene:methanol in the ration of 3:1:1. The solution is passed through a column of Sephadex LH-20 (having a 30 centimeter diameter) in the above solvent taking fractions at the rate of 250 ml. per minute. After two 20-liter portions of the solvent mixture are collected and discarded, a forecut of 10 liters is taken and discarded. Then 30 rich cuts of 2 liters each are taken. Fractions 1–13 and 25–30 are discarded. Fractions 14–16 are combined an contain 20 g. of predominately C-076 B1a. Fractions 22–24 are combined and contain 6.7 g. of approximately 30% C-076 B1b. Fractions 17–20 contain a mixture of C-076 B1a and B1b.

Fractions 17–20 above are combined and concentrated and passed through a Sephadex LH-20 column with the same solvent system as above. Three 20-liter forecuts are taken and discarded. Rich cuts are then taken as follows: 5 cuts of 2 liters each (fractions 1–5); 20 cuts of 1 liter each (fractions 6–25); and 10 cuts of 2 liters each (fractions 26–35). Fractions 1–15 are discarded; fractions 16–21 contain 13.5 g. of C-076 B1a and 0.4 g. of C-076 B1b; fractions 22–26 contain 44 g. of C-076 B1a and 0.31 g. of C-076 B1b; fractions 27–30 contain 10.2 g. of C-076 B1a and 0.8 g. of C-076 B1b.

EXAMPLE 4

A column of Sephadex LH-20 is washed with hexane:toluene:methanol 3:1:1 overnight at 0.28 ml./min. to equilibrate the resin. Final bed volume is 53 ml. (1.3 cm. diam. ×40 cm. height). A 62-mg. sample of mixed C-076 B1 and B2 is dissolved in 1 ml. of solvent mixture, applied to the column and developed at 0.28 ml./min.

The composition by high pressure liquid chromatography (HPLC) assay is:
B2a: 52.4%
B1a: 44.7%
B1b: 2.7%
B2b: 0.2%

Column effluent is collected in fractions, the first 25 ml., then every 5 minutes automatically. A 2-μl. aliquot of each fraction is spotted on a TLC plate containing phosphor to determine which fractions contain UV absorbing compounds. Fractions 12 through 26 are selected for further investigation by TLC and total solids. A 5-μl. aliquot of each fraction is spotted on a 20×20 cm. TLC plste (Silica-Gel 60-F254, E. M. Laboratories Inc., 500 Exec. Blvd., Elmsford, NY 10523). The spots are dried and the plate is then developed with chloroform:ethyl acetate:methanol 9:9:1. The plate is examined under short-wave UV light and identification of the components in each fraction is made by comparison to a reference sample run on the same plate.

Fractions 12 through 17 contained C-076 B1, while fractions 21 through 26 contained C-076 B2. Fractions 18 through 20 contained mixtures of B1 and B2, however, total solids determinations on each fraction indicate that these fractions contain only a small portion of the total amout charged.

The recoveries and elution volumes of the two major components are tabulated below.

|  | Elution Volume | Recovery |
|---|---|---|
| C-076 B1 | 0.87 column volume | 89% |
| C-076 B2 | 1.05 column volume | 68% |

EXAMPLE 5

A sample of 200 mg. of crude C-076 is dissolved in 0.8 ml. of a solvent mixture of hexane:toluene:methanol in the ratio of 6:1:1. The solvent mixture is chromatographed on a column 1.27 cm. ×65 cm. containing Sephadex LH-20 as the packing. The column is eluted with a solvent mixture of hexane:toluene:methanol in a 6:1:1 ratio at a flow rate of 2 ml. per 5 minutes with 2-ml. cuts being taken. Five (5) microliters of each cut is applied to E. Merck silica-gel 60-F254 plate and the C-076 components determined by thin layer chromatography (tlc) with a 10:10:1:2 system (chloroform:ethyl acetate:methyl alcohol:methylene chloride). Based on the tlc results, the cuts are pooled as shown in Table I as assayed using high pressure liquid chromatography assay techniques.

TABLE I

| Sample No. | Volume | Yield (mg.) | HPLC Assay (%) | | |
|---|---|---|---|---|---|
|  |  |  | A1a | A1b | A2a |
| Feed | 0.8 ml. | 200 | 71.9 | 12.3 | 13.7 |
| 1 | 60–116 ml. | 164.4 | 82.8 | 15.2 | 0.9 |
| 2 | 128–146 ml. | 22.4 | 1.4 | 0.4 | 95.7 |

Sephadex is a tradename given to dextran gels which are natural polymers of glucose made by fermentation and cross-linked with epichlorohydrin.

Although the hydroxy propylated dextran gels are the preferred packing utilized in this invention, other derivatives that might be utilized are the nitro alkyl, cyano alkyl or other derivatives of the alkyls that would exhibit similar properties as the hydroxy propylated dextran gel.

What is claimed is:

1. A process for the preparation of C-076 B1 and B2 components, wherein said C-076 B1 and B2 components have the structure:

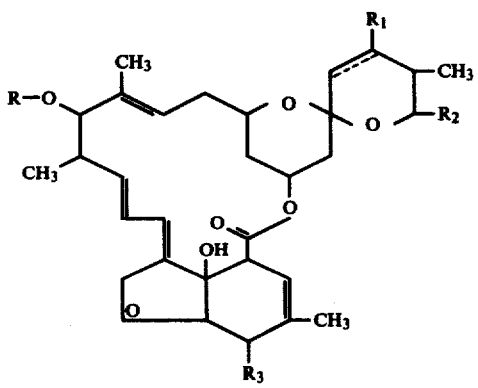

wherein
R is:

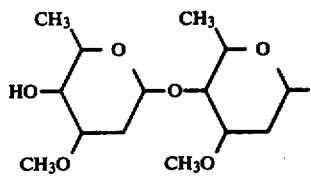

and wherein the broken line indicates a single or a double bond; $R_1$ is hydroxy and is present only when said broken line indicates a single bond;

$R_2$ is propyl or butyl; and $R_3$ is hydroxy, from a solution containing a mixture of said C-076 B1 and B2 components obtained from the extraction of the fermentation broth of a C-076 producing strain of *Streptomyces avermitilis*, wherein said solution is chromatographed on a column containing hydroxyalkylated dextran gel and eluting said components with a solvent mixture of low boiling hydrocarbons: toluene, benzene or xylene: lower alcohols in the ratio of 30–90:10–60:5–25 and recovering said components.

2. A process for the separation of C-076 A1 and A2 components, wherein said C-076 A1 and A2 components have the structure:

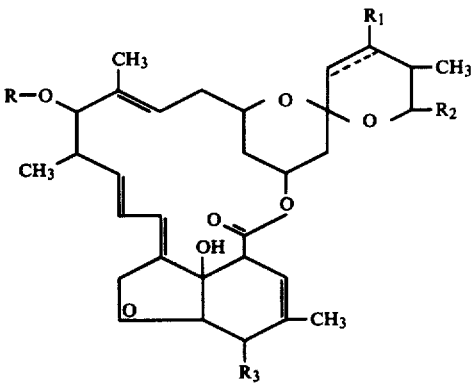

wherein R is:

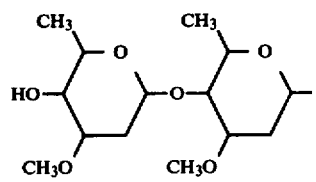

and wherein the broken line indicates a single or a double bond; $R_1$ is hydroxy and is present only when said broken line indicates a single bond;

$R_2$ is propyl or butyl; and

R is methoxy, from a solution containing a mixture of said C-076 A1 and A2 components obtained from the extraction of the fermentation broth of a C-076 producing strain of *Streptomyces avermitilis* wherein said solution is chromatographed on a column containing hydroxyalkylated dextran gel and eluting said components with a solvent mixture of low boiling hydrocarbons: toluene, benzene or xylene: lower alcohols at a ration of 5–7:0.5–1.5: 0.5–1.5 and recovering said components.

3. A process according to claim 1 wherein the low boiling hydrocarbon is selected from the group of pentane, hexane, heptane, octane and isopentane; and the lower alcohol is selected from the group consisting of methanol, ethanol, propanol and isopropanol.

4. A process according to claim 2 wherein the low boiling hydrocarbon is selected from the group of pentane, hexane, heptane, octane and isopentane; and the lower alcohol is selected from the group consisting of methanol, ethanol, propanol and isopropanol.

5. A process according to claim 3 wherein the solvent mixture is hexane:toluene:methanol in a ration of 3:1:1.

6. A process according to claim 4 wherein a solvent mixture is hexane:toluene:methanol in a ratio of 6:1:1.

* * * * *